(12) United States Patent
Kumita et al.

(10) Patent No.: US 9,193,662 B2
(45) Date of Patent: Nov. 24, 2015

(54) METHOD FOR PRODUCING MIXTURE CONTAINING FATTY ACID MONOGLYCERIDE

(71) Applicant: KAO CORPORATION, Tokyo (JP)

(72) Inventors: Yasukazu Kumita, Wakayama (JP); Takeshi Shirasawa, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 14/355,237

(22) PCT Filed: Dec. 7, 2012

(86) PCT No.: PCT/JP2012/081783
§ 371 (c)(1),
(2) Date: Apr. 30, 2014

(87) PCT Pub. No.: WO2013/085031
PCT Pub. Date: Jun. 13, 2013

(65) Prior Publication Data
US 2014/0303388 A1    Oct. 9, 2014

(30) Foreign Application Priority Data
Dec. 8, 2011    (JP) .................................. 2011-269137

(51) Int. Cl.
C07C 67/08    (2006.01)
C07C 67/03    (2006.01)
C11C 3/06    (2006.01)

(52) U.S. Cl.
CPC ................ *C07C 67/08* (2013.01); *C07C 67/03* (2013.01); *C11C 3/06* (2013.01)

(58) Field of Classification Search
None
See application file for complete search history.

(56) References Cited

U.S. PATENT DOCUMENTS

| | | | |
|---|---|---|---|
| 2,909,540 A | 10/1959 | Woods | |
| 3,079,412 A | 2/1963 | Chang et al. | |
| 3,083,216 A * | 3/1963 | Alsop et al. .................... | 554/168 |
| 3,102,129 A * | 8/1963 | Birnbaum et al. ............. | 554/157 |
| 5,399,731 A | 3/1995 | Wimmer | |
| 2007/0129560 A1 | 6/2007 | Sawada et al. | |

FOREIGN PATENT DOCUMENTS

| | | |
|---|---|---|
| CN | 86104493 A | 11/1987 |
| CN | 101092589 A | 12/2007 |
| CN | 101691525 A | 4/2010 |
| CN | 102241586 A | 11/2011 |

(Continued)

OTHER PUBLICATIONS

DE 3020566, Guenther, D. et al., Process for the continuous production of fatty-acid monoglycerides, 1981, 7 pages, English translation.*

(Continued)

*Primary Examiner* — Yate K Cutliff
(74) *Attorney, Agent, or Firm* — Birch, Stewart, Kolasch & Birch, LLP

(57) ABSTRACT

The present invention relates to a method for producing a mixture containing fatty acid monoglyceride from glycerin and a compound having at least one acyl group, selected from fatty acids and fatty acid glycerides, including: (i) a step of obtaining a mixture containing fatty acid monoglyceride by heating and reacting glycerin and a compound having at least one acyl group, selected from fatty acids and fatty acid glycerides in the presence of a catalyst; (ii) a step including adding glycerin, which is liquid and has a lower temperature than the temperature of the mixture, to the mixture to cool the mixture; and (iii) a step of separating the mixture containing fatty acid monoglyceride from glycerin, obtained in the step (ii), by separating layers.

20 Claims, 1 Drawing Sheet

(56) References Cited

FOREIGN PATENT DOCUMENTS

| DE | 3020566 | * | 12/1981 | ............. C07C 67/03 |
|---|---|---|---|---|
| EP | 0 041 204 A1 | | 12/1981 | |
| JP | 57-24327 A | | 2/1982 | |
| JP | 2001-31991 A | | 2/2001 | |
| JP | 2004-359885 A | | 12/2004 | |

OTHER PUBLICATIONS

JP 2004-359885, Sawada, H. et al., Manufacturing method of monoglyceride-containing composition, 2004, 7 pages, English translaiton.*

International Search Report, issued in PCT/JP2012/081783, dated Feb. 26, 2013.

Written Opinion of the International Search Authority, issued in PCT/JP2012/081783, dated Feb. 26, 2013.

International Preliminary Report on Patentability and English translation of the Written Opinion of the International Searching Authority dated Jun. 10, 2014 for International Application No. PCT/JP2012/081783.

The Office Action (including an English translation), dated Apr. 21, 2015, issued in the corresponding Chinese Patent Application No. 201280060675.4.

* cited by examiner

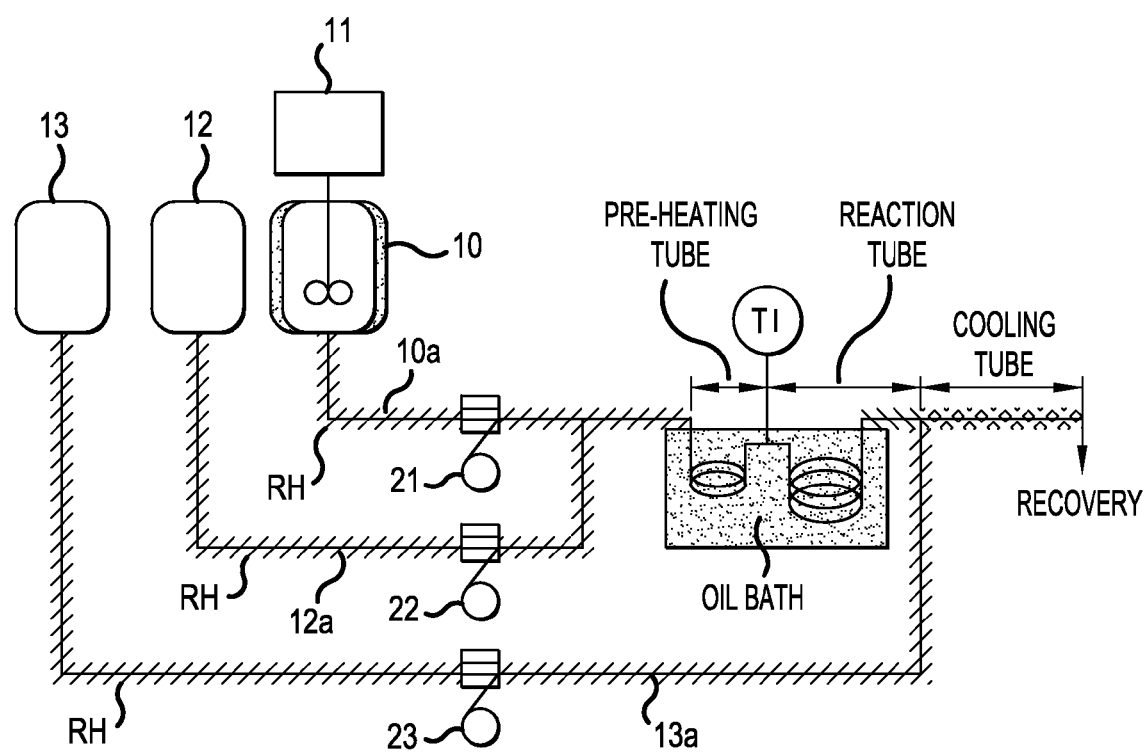

METHOD FOR PRODUCING MIXTURE CONTAINING FATTY ACID MONOGLYCERIDE

FIELD OF THE INVENTION

The present invention relates to a method for producing a mixture containing fatty acid monoglyceride.

BACKGROUND OF THE INVENTION

Fatty acid monoglycerides used widely as an oil agent and the like in cosmetics, foods, and industrial emulsifiers or lubricants are produced by esterification reaction of glycerin with fatty acid or by ester exchange reaction of glycerin with fat and oil.

Those reactions are carried out in the absence or presence of a catalyst, and generally a mixture of glycerin, fatty acid monoglyceride, fatty acid diglyceride, and fatty acid triglyceride is generated.

For such reasons, a purification step is required depending on a purpose. When it is desired to obtain a fatty acid monoglyceride with high purity, purification based on molecular distillation or thin layer distillation is performed. Fatty acid diglyceride and fatty acid triglyceride contained in residuals after distillation of monoglyceride can be recovered again as monoglyceride according to a transesterification reaction with glycerin. However, from the viewpoint of production efficiency of monoglyceride, higher purity of the monoglyceride before distillation step is preferred.

As disclosed in JP-A 57-24327, it is known that the equilibrium of the ester exchange reaction shifts to the fatty acid monoglyceride production side as the reaction temperature increases. By maintaining fat and glycerin as a raw material at high temperature like 220° C. or higher in the presence of a catalyst, concentration of the fatty acid monoglyceride increases.

However, when time is required for cooling in the presence of a catalyst, it is known that the reaction toward the equilibrium at that temperature, that is, the reaction from two molecules of fatty acid monoglyceride to fatty acid diglyceride and glycerin, becomes larger, so that the concentration of fatty acid monoglyceride is decreased.

It is then disclosed in JP-A 57-24327 to neutralizing an alkali catalyst with an acid, after completion of the reaction, to inactivate it, decrease the reaction rate and prevent the concentration of fatty acid monoglyceride from decreasing.

It is disclosed in U.S. Pat. No. 2,909,540 to prevent the concentration of fatty acid monoglyceride from decreasing by lowering the reaction rate by evaporating glycerin at a reduced pressure, after the reaction for producing fatty acid monoglyceride, and cooling the liquid of the completed reaction with heat transfer accompanied with evaporation.

In U.S. Pat. No. 3,083,216, production of higher fatty acid monoglyceride is disclosed. In U.S. Pat. No. 3,079,412, continuous production of fatty acid monoglyceride is disclosed.

SUMMARY OF THE INVENTION

The present invention relates to a method for producing a mixture containing fatty acid monoglyceride from glycerin and a compound having at least one acyl group, selected from fatty acids and fatty acid glycerides, including:

(i) a step of obtaining a mixture containing fatty acid monoglyceride by heating and reacting glycerin and a compound having at least one acyl group, selected from fatty acids and fatty acid glycerides in the presence of a catalyst, (ii) a step including adding glycerin, which is liquid and has a lower temperature than the temperature of the mixture, to the mixture to cool the mixture, and (iii) a step of separating the mixture containing fatty acid monoglyceride from glycerin, obtained in the step (ii), by separating layers.

BRIEF DESCRIPTION OF DRAWINGS

FIG. 1 is a schematic diagram illustrating a production apparatus used in Example 5.

DETAILED DESCRIPTION OF THE INVENTION

According to JP-A 57-24327, salts are produced by neutralization and facilities for purification like filtration are required to remove the produced salts. Further, according to U.S. Pat. No. 2,909,540, the reaction equilibrium is disturbed and shifts to the side of having decomposition of fatty acid monoglyceride, and thus it is impossible to produce a mixture containing fatty acid monoglyceride having a large content of the fatty acid monoglyceride.

Under the circumstances, provided by the present invention is a method for producing a mixture containing fatty acid monoglyceride with a high content of fatty acid monoglyceride.

According to the present invention, a mixture containing fatty acid monoglyceride with a high content of fatty acid monoglyceride can be produced at the final stage of the reaction step, the purification load thereafter can be reduced, and the production amount of monoglyceride per hour can be increased.

The method for producing a mixture containing fatty acid monoglyceride of the present invention (in contrast to the one obtained from the step (i), it may be referred to as a "final mixture") includes (i) a step of obtaining a mixture containing fatty acid monoglyceride (intermediate mixture) by heating and reacting glycerin and a compound having at least one acyl group, selected from fatty acids and fatty acid glycerides, (hereinbelow, it may be referred to as a "compound having an acyl group") in the presence of a catalyst, (ii) a step including adding glycerin, which is liquid and has a lower temperature than the temperature of the mixture, to the mixture to cool the mixture, and (iii) a step of separating the mixture containing fatty acid monoglyceride and glycerin, obtained in the step (ii), by separating layers.

Meanwhile, each of the reaction mode of the step (i) and the cooling mode of the step (ii) can be any of a batch mode and a continuous mode. In case of a batch mode, it can be any of a batch type and a semi-batch type.

<Step (i) Step for Obtaining a Mixture Containing Fatty Acid Monoglyceride>

The compound having an acyl group used in the step (i) of the present invention may have any of branched, linear, saturated, and unsaturated acyl groups, but from the viewpoint of a more evident effect of the present invention, the number of carbon atoms in the acyl group is preferably 8 to 30, more preferably 12 to 22, and even more preferably 14 to 18. From the same point of view, the number of carbon atoms in the acyl group of the compound having an acyl group used in the step (i) of the present invention is preferably 8 or more, 12 or more, or 14 or more, and also 30 or less, 22 or less, or 18 or less.

Specific examples of the fatty acid in the compound having an acyl group which is used in the present invention include capronic acid, caprylic acid, capric acid, lauric acid, myristic acid, palmitic acid, stearic acid, eicosanoic acid, behenic acid, oleic acid, elaidic acid, linoleic acid, linolenic acid, soybean oil fatty acid, rapeseed oil fatty acid, and tall oil fatty acid.

Examples of the fatty acid glyceride in the compound having an acyl group used in the invention include triester and a diester containing fatty acid and glycerin as a constitutional component, and a mixture thereof. There is no problem of containing monoester therein.

Specific examples thereof include coconut oil, palm oil, palm seed oil, soybean oil, rapeseed oil, beef tallow, lard, tall oil, and fish oil.

With regard to the reaction ratio between glycerin and the compound having an acyl group, from the viewpoint of obtaining a mixture containing fatty acid monoglyceride with a high content of fatty acid monoglyceride and increasing the productivity per batch or unit time, glycerin is preferably 1.0 to 5.0 mol, more preferably 1.3 to 4.0 mol, and even more preferably 2.0 to 3.0 mol per mol of an acyl group in the compound having an acyl group. With regard to the reaction ratio between glycerin and the compound having an acyl group, from the same point of view, glycerin is preferably 1.0 mol or more, 1.3 mol or more, or 2.0 mol or more, and also 5.0 mol or less, 4.0 mol or less, or 3.0 mol or less per mol of an acyl group in the compound having an acyl group The temperature for the reaction between glycerin and the compound having an acyl group is, from the viewpoint of enhancing the solubility of glycerin in an oil layer and increasing the rate of esterification reaction and ester exchange reaction, preferably 200° C. or higher, more preferably 210° C. or higher, and even more preferably 215° C. or higher. From the viewpoint of suppressing production of diglycerin as a byproduct, it is preferably 400° C. or less, more preferably 350° C. or less, and even more preferably 300° C. or less. From the same point of view, it is preferably 200 to 400° C., more preferably 210 to 350° C., and even more preferably 215 to 300° C.

The time for the reaction between glycerin and the compound having an acyl group depends on the reaction temperature and the kind and the amount of the used catalyst or the like. From the viewpoint of enhancing the yield of fatty acid monoglyceride by surely reaching near the reaction equilibrium, it is preferably 5 minutes or longer, more preferably 1 hour or longer, and even more preferably 2 hours or longer. Further, from the viewpoint of the byproduct amount of diglycerin as a condensation of glycerin, it is preferably 12 hours or shorter, more preferably 10 hours or shorter, and even more preferably hours or shorter. Meanwhile, confirmation of the end point can be made by suitably collecting a sample and analyzing it. For example, it can be made by confirming no change in the content of monoglyceride.

The step for obtaining the mixture containing fatty acid monoglyceride (intermediate mixture) of the present invention is performed in the presence of a catalyst. Examples of the catalyst include the catalysts that are used for an esterification reaction or an ester exchange reaction.

From the viewpoint of enhancing the yield of fatty acid monoglyceride by dispersing the mixture in a more homogenous state, a catalyst soluble in fatty acid glyceride and glycerin is preferable. Specifically, an alkali metal hydroxide or an alkaline earth metal hydroxide is preferable. Sodium hydroxide, potassium hydroxide, or calcium hydroxide is more preferable. Calcium hydroxide is even more preferable.

From the viewpoint of ensuring the sufficient rate of esterification reaction and ester exchange reaction, the catalyst concentration is preferably 1 ppm (based on mass) or more. More preferably, it is 10 ppm or more. Even more preferably, it is 50 ppm or more. From the viewpoint of increase of the yield of fatty acid monoglyceride by suppressing the reaction from two molecules of fatty acid monoglyceride to fatty acid diglyceride and glycerin during cooling (hereinbelow, referred to as a reverse reaction), the catalyst concentration is preferably 1000 ppm or less, more preferably 750 ppm or less, and even more preferably 500 ppm or less. In the present invention, after adding the catalyst to glycerin and the compound having an acyl group and adjusting the catalyst concentration preferably to the aforementioned range, the step (i) and the step (ii) are performed.

<Step (ii): Step Including Adding Glycerin to a Mixture Containing Fatty Acid Monoglyceride for Cooling>

The step (ii) of the present invention is a step in which, in addition to cooling the reaction product of the step (i) (intermediate mixture) by adding glycerin, a catalyst concentration in the liquid phase is lowered by adding glycerin and, by extracting the catalyst contained in the intermediate mixture, the reverse reaction is suppressed.

The temperature of the mixture obtained from the step (i) is preferably the reaction temperature of the step (i). The temperature of the mixture is preferably 200° C. or higher, more preferably 210° C. or higher, and even more preferably 215° C. or higher, and also preferably 400° C. or lower, more preferably 350° C. or lower, and even more preferably 300° C. or lower. Specifically, it is preferably 200 to 400° C., more preferably 210 to 350° C., and even more preferably 215 to 300° C.

The step (ii) has lower temperature than the mixture of the step (i), and also liquid glycerin is added thereto.

Temperature of glycerin (boiling point: 280° C.) added in the step (ii) is, from the viewpoint of cooling the reaction product (intermediate mixture) of the step (i), preferably 180° C. or lower, more preferably 100° C. or lower, and even more preferably 50° C. or lower within the range in which the aforementioned temperature is satisfied.

Further, from the viewpoint of fluidity, it is preferably 0° C. or higher, more preferably 10° C. or higher, and even more preferably 20° C. or higher.

The addition amount of glycerin in the step (ii) is, from the viewpoint of preventing the reverse reaction, preferably 1 part by mass or more, more preferably 10 parts by mass or more, and even more preferably 50 parts by mass or more per 100 parts by mass of the mixture containing fatty acid monoglyceride (intermediate mixture).

An addition amount of glycerin in the step (ii) is, from the viewpoint of the capacity of a separation tank and a storage tank that are required for layer separation of the composition layer containing fatty acid monoglyceride and glycerin layer, preferably 1000 parts by mass or less, more preferably 500 parts by mass or less, and even more preferably 150 parts by mass or less per 100 parts by mass of the mixture containing fatty acid monoglyceride (intermediate mixture).

From the same point of view, the addition amount of glycerin in the step (ii) is preferably 1 to 1000 parts by mass, more preferably 10 to 500 parts by mass, and even more preferably 50 to 150 parts by mass per 100 parts by mass of the mixture containing fatty acid monoglyceride (intermediate mixture).

An addition amount of glycerin in the step (ii) is, from the viewpoint of preventing the reverse reaction, preferably $1\times10^3$ parts by mass or more, more preferably $1\times10^4$ parts by mass or more, and even more preferably $1\times10^5$ parts by mass or more per 100 parts by mass of the catalyst.

The addition amount of glycerin in the step (ii) is, from the viewpoint of the size of a separation tank and a storage tank that are required for layer separation of the composition layer containing fatty acid monoglyceride and glycerin layer, preferably $1\times10^9$ parts by mass or less, more preferably $5\times10^7$ parts by mass or less, and even more preferably $3 \times 10^6$ parts by mass or less per 100 parts by mass of the catalyst.

From the same point of view, the addition amount of glycerin in the step (ii) is preferably $1 \times 10^3$ to $1 \times 10^5$ parts by mass, more preferably $1 \times 10^4$ to $5 \times 10^7$ parts by mass, and even more preferably $1 \times 10^5$ to $3 \times 10^5$ parts by mass per 100 parts by mass of the catalyst.

Rate of cooling the mixture in the step (ii) is, from the viewpoint of preventing the reverse reaction, preferably 1° C./minute or higher, more preferably 5° C./minute or higher, even more preferably 8° C./minute or higher, even more preferably 50° C./minute or higher, and even more preferably 100° C./minute or higher. From the viewpoint of the energetic load, it is preferably 1000° C./minute or lower, more preferably 500° C./minute or lower, and even more preferably 300° C./minute or lower.

In the step (ii), the cooling rate in a region with higher mixture temperature has a greater influence on having improved yield of fatty acid monoglyceride. In the present invention, adding glycerin at the cooling rate within the aforementioned range to the mixture at the temperature of 100° C. or higher, or 140° C. or higher followed by cooling is preferable in that it has a significant effect of preventing the reverse reaction. Further, in the step (ii) of the present invention, it is preferable to add glycerin at the cooling rate within the aforementioned range until the temperature of the mixture is 140° C. or lower, or 100° C. or lower and do cooling, because the effect of prevention of the reverse reaction is remarkable.

Further, the temperature of the mixture after cooling in the step (ii) is, from the viewpoint of efficiently performing layer separation while preventing solidification of the mixture, preferably 80° C. or higher and more preferably 90° C. or higher and also preferably 200° C. or lower, more preferably 180° C. or lower, and even more preferably 150° C. or lower.

It is preferable that the addition of glycerin be performed under mixing such that the cooling rate of the entire mixture is within the aforementioned range. As for the method for mixing, a conventionally known method can be used.

When the step (ii) is performed in a batch mode reaction by using the stirring tank type reactor, glycerin is added under stirring the mixture such that the cooling rate of the entire mixture is within the aforementioned range.

As for stirring wings of a stirrer, a stirring wing such as a three-piece swept wing, a full zone wing, a turbine wing, or a max blend wing can be used.

The stirring power required per unit volume of the fluid in the reactor is, from the viewpoint of cooling the entire mixture, preferably 0.1 kW/m$^3$ or higher, more preferably 0.5 kW/m$^3$ or higher, and even more preferably 2 kW/m$^3$ or higher. Further, from the viewpoint of the energy load, it is preferably 200 kW/m$^3$ or lower, more preferably 100 kW/m$^3$ or lower, and even more preferably 50 kW/m$^3$ or lower.

As described herein, the "stirring power required per unit volume" is a value obtained by calculating a difference between the measured value of stirring power during reaction (unit: kW) and the measured value of idling power before adding the raw materials for the reaction (unit kW) and dividing the result by the volume of fluid in the reactor (unit: m$^3$).

Further, addition of glycerin can be either continuous or intermittent as long as the cooling rate of the entire mixture is within the aforementioned range.

The cooling rate corresponds to the temperature-decreasing amount per unit time. When the step (ii) is performed continuously in a tubular reactor, the cooling rate can be a value which is obtained by dividing the temperature difference between the entrance and exit of the cooling part by a value obtained by dividing a flow passage length by a linear velocity.

When the step (ii) is continuously performed in a tubular reactor, from the viewpoint of having the cooling rate of the entire mixture within the aforementioned range, mixing the mixture obtained from the step (i) with glycerin is performed at a shear rate U/Dmin of preferably 1 (1/see) or more, more preferably 10 (1/sec) or more, and even more preferably 100 (1/sec) or more. From the viewpoint of the energy load, it is performed at a shear rate U/Dmin of preferably 100000 (1/sec) or less, more preferably 50000 (1/sec) or less, and even more preferably 10000 (1/sec) or less.

Regarding the shear rate U/Dmin, Dmin represents minimum inner diameter (mm) of the flow passage in the mixing part and U represents a linear velocity (mm/sec) of the mixture at Dmin. Meanwhile, when the flow amount of the mixture is Q (mL/sec), U (mm/sec) can be obtained based on the following Equation (1). In the equation, n represents the number of minimum inner diameter of the flow passage, and when a contraction type stirrer of a porous plate is used, for example, it represents the number of pores in the stirrer.

$$U(\text{mm/sec}) = Q \times 1000 / (n \times \pi \times (D\text{min})^2 / 4) \tag{1}$$

Cross-sectional shape of the mixing part is not necessarily required to be a circle. When it is a shape other than a circle, U means the flow rate in the minimum cross sectional area of the flow passage. In such case, the diameter of a circle having the same area as the minimum cross sectional area of the flow passage is used for Dmin.

<Step (iii): Step for Separating a Mixture Containing Fatty Acid Monoglyceride and Glycerin by Layer Separation>

After the step (ii), a step of separating the mixture containing fatty acid monoglyceride and glycerin by separating layers is performed as the step (iii).

As for the separation method of the step (iii) by separating layers, a method conventionally known as a method for separating a mixture containing fatty acid monoglyceride and glycerin can be used. Specific examples thereof include stationary separation and centrifugal separation.

From the viewpoint of the energy efficiency and simplification of facilities, stationary separation and centrifugal separation are preferable, and stationary separation is more preferable.

Specific examples of the stationary separation include allowing the mixture obtained from the step (ii) to stand in a storage tank and then using a separation device, such as an API type oil separator, a CPI type oil separator or a PPI type oil separator.

Examples of the centrifugal separator include De Laval type centrifuge and sharpless type centrifuge.

Further, from the viewpoint of efficiently performing the layer separation with prevention of solidification of mixture, temperature of the mixture with a mixture containing fatty acid monoglyceride and glycerin, which is subjected to layer separation in the step (iii), is preferably 80° C. or higher and more preferably 90° C. or higher and also preferably 200° C. or lower, more preferably 180° C. or lower, and even more preferably 150° C. or lower.

From the viewpoint of the stability of fatty acid monoglyceride in the mixture to be obtained, the concentration of the alkali catalyst remaining in the mixture containing fatty acid monoglyceride, obtained in the step (iii), is 0.1% by mass or less, preferably 100 ppm or less.

Glycerin separated in the step (iii) can be used in the step (i) or the step (ii), and preferably in the step (i).

Aspects and preferred embodiments of the present invention are described hereinbelow.

<1>

A method for producing a mixture containing fatty acid monoglyceride from glycerin and a compound having at least one acyl group, selected from fatty acids and fatty acid glycerides, including:

(i) a step of obtaining a mixture containing fatty acid monoglyceride by heating and reacting glycerin and a compound having at least one acyl group, selected from fatty acids and fatty acid glycerides, in the presence of a catalyst, (ii) a step including adding glycerin to the mixture and cooling the mixture, adding liquid glycerin having a temperature lower than the temperature of the mixture, and (iii) a step of separating the mixture containing fatty acid monoglyceride and glycerin, obtained in the step (ii), by separating layers.

<2>

The method for producing a mixture containing fatty acid monoglyceride described in <1> above, in which an addition amount of glycerin in the step (ii) is preferably 1 part by mass or more, more preferably 10 parts by mass or more, and even more preferably 50 parts by mass or more and also preferably 1000 parts by mass or less, more preferably 500 parts by mass or less, and even more preferably 150 parts by mass or less per 100 parts by mass of the mixture containing fatty acid monoglyceride obtained from the previous step.

<3>

The method for producing a mixture containing fatty acid monoglyceride described in <1> or <2> above, in which the rate of cooling the mixture in the step (ii) is preferably 1° C./minute or higher, more preferably 5° C./minute or higher, even more preferably 8° C./minute or higher, even more preferably 50° C./minute or higher, and even more preferably 100° C./minute or higher and also preferably 1000° C./minute or lower, more preferably 500° C./minute or lower, and even more preferably 300° C./minute or lower.

<4>

The method for producing a mixture containing fatty acid monoglyceride described in any of <1> to <3> above, in which the addition amount of glycerin in the step (ii) is preferably $1 \times 10^3$ parts by mass or more, more preferably $1 \times 10^4$ parts by mass or more, and even more preferably $1 \times 10^5$ parts by mass or more and also preferably $1 \times 10^9$ parts by mass or less, more preferably $5 \times 10^7$ parts by mass or less, and even more preferably $3 \times 10^6$ parts by mass or less per 100 parts by mass of the catalyst used in the previous step.

<5>

The method for producing a mixture containing fatty acid monoglyceride described in any of <1> to <4> above, in which the reaction temperature in the step (i) is preferably 200° C. or higher, more preferably 210° C. or higher, even more preferably 215° C. or higher, and also preferably 400° C. or lower, even more preferably 0.350° C. or lower, and even more preferably 300° C. or lower.

<6>

The method for producing a mixture containing fatty acid monoglyceride described in any of <1> to <5> above, in which the temperature of glycerin to be added in the step (ii) is preferably 0° C. or higher, more preferably 10° C. or higher, and even more preferably 20° C. or higher and also preferably 180° C. or lower, more preferably 100° C. or lower, and even more preferably 50° C. or lower.

<7>

The method for producing a mixture containing fatty acid monoglyceride described in any of –1> to <6> above, in which catalyst concentration of the catalyst used in step (i) is preferably 1 ppm or more, more preferably 10 ppm or more, and even more preferably 50 ppm or more, and also preferably 1000 ppm or less, more preferably 750 ppm or less, and even more preferably 500 ppm or less.

<8>

The method for producing a mixture containing fatty acid monoglyceride described in any of <1> to <7> above, in which separation method of the step (iii) by separating layers is stationary separation.

<9>

The method for producing a mixture containing fatty acid monoglyceride described in any of –1> to <8> above, in which temperature of the mixture in the step (ii) is preferably 100° C. or higher and more preferably 140° C. or higher, and the rate of cooling the mixture in the step (ii) is preferably 1° C./minute or higher, more preferably 5° C./minute or higher, even more preferably 8° C./minute or higher, even more preferably 50° C./minute or higher, and even more preferably 100° C./minute or higher and preferably 1000° C./minute or lower, more preferably 500° C./minute or lower, even more preferably 300° C./minute or lower.

EXAMPLES

Hereinbelow, the present invention is described more in details by reference to Examples and Comparative Examples. Example is set forth for examples of the present invention and does not limit the present invention.

[Method for Analyzing Fatty Acid Monoglyceride]

Dodecane as an internal standard material was weighed and added to a sample containing fatty acid monoglyceride and mixed therein. Meanwhile, when layer separation is performed for the reaction product of the Examples and the Comparative Examples, the sample was collected from an oily layer separated on an upper part.

A trimethylsilylating agent (trade name: TMSI-H, manufactured by GL Sciences, Inc.) was added to the mixture and then was heated and stirred. After dilution with hexane, the solid matter was separated by filtration and the obtained filtrate was subjected to gas chromatography analysis according to the following conditions.

Apparatus: 6890N Network GC System, manufactured by Agilent Technologies

Column: Ultra ALLOY-1 (MS/HT), manufactured by Frontier Laboratories Ltd., length 30 m×inner diameter 0.25 mm×film thickness 0.15 μm Detector: FID Condition for temperature increase: 60° C. (kept for 2 minutes)→10° C./minute→350° C. (kept for 15 minutes)

Injection temperature: 300° C.

Detector temperature: 350° C.

Preparation Example 1

Glycerin monostearic acid (monoglyceride content: 98% by mass) (300 g) was dissolved at 90° C., added with 0.27 g of 48% by mass aqueous sodium hydroxide solution, and stirred for 30 minutes to obtain glycerin monostearic acid containing the adjusted catalyst amount. The glycerin monostearic acid used in this case can be synthesized according to the following method.

Hydrogenated palm oil, glycerin, and glycerin containing dispersed calcium hydroxide were continuously fed to a reactor so as to have a flow amount ratio that glycerin is 0.9 mol per mol of the ester group of the hydrogenated palm oil and calcium hydroxide is 0.01% by mass per mass of hydrogenated palm oil and glycerin, and the reaction was allowed to occur at 250° C. Subsequently, under reduced pressure condition, removal of low boiling point components in the reaction solution and distillation removal of unreacted glycerin in the reaction solution were performed. Subsequently, the mixture containing monoglyceride as a main component was separated by distillation. By distilling the remaining glycerin out of the separated mixture, glycerin monostearic acid used in Preparation Example 1 can be produced.

Reference Example 1

It was confirmed that, when the step (ii) of the production method of the present invention is performed by using glycerin monostearic acid (manufactured by Wako Pure Chemical Industries, Ltd., glycerol monostearic acid, monoglyceride content: 56% by mass) as a starting material, decomposition of the monoglyceride is suppressed so that a mixture having a high content of fatty acid monoglyceride is obtained.

To a 100-mL four-neck flask equipped with a stirrer and a thermometer, 25.0 g of the glycerin monostearic acid and 0.0026 g of calcium hydroxide (manufactured by Kanto Chemical Co., Inc.) were fed and the temperature was raised to 100° C. After dissolving glycerin monostearic acid, inside of the flask was stirred at 300 r/min so that calcium hydroxide can also homogeneously get dissolved.

After that, the flask was removed from the oil bath, and only the oil bath was heated to 220° C. After confirming that the oil bath temperature is stabilized, the flask was placed in the oil bath and the temperature of the content was increased to 215° C. while inside of the flask was stirred at 300 r/min. Once the temperature reaches 215° C., the stirring was temporarily stopped and a sample for analysis was taken, which was used as an intermediate mixture before cooling.

After that, the stirring was resumed and 25.2 g of glycerin (manufactured by Kishida Chemical. Co., Ltd.), which has been preheated to 100° C., was added over five minutes while control is made such that the rate for cooling the content is almost constant over time. During and after addition of glycerin, the flask was partially or completely removed from the oil bath. The cooling rate at that time remained constant during and after the addition of glycerin, being 8° C./min. According to the addition of glycerin, the intermediate mixture was cooled to 175° C.

Even after completion of the addition of glycerin, cooling was continued until the temperature of the content becomes 140° C. After maintaining at 140° C. for 30 minutes, the stirring was temporarily terminated and a sample for analysis was taken from the upper layer, which was used as a final mixture after cooling. As a result of stopping the stirring, the content was separated into layers. In Table 1, operating conditions (feeding amount of monoglyceride or the like) and the decomposition ratio of monoglyceride are listed.

Reference Example 2

To a 100-mL four-neck flask equipped with a stirrer and a thermometer, 25.0 g of the glycerin monostearic acid (glycerol monostearic acid manufactured by Wako Pure Chemical Industries, Ltd., monoglyceride content: 56% by mass) and 0.0025 g of calcium hydroxide (manufactured by Kanto Chemical Co., Inc.) were fed and the temperature was raised to 100° C. After dissolving glycerin monostearic acid, inside of the flask was stirred at 300 r/min so that calcium hydroxide can also homogeneously get dissolved.

After that, the flask was removed from the oil bath, and only the oil bath was heated to 220° C. After confirming that the oil bath temperature is stabilized, the flask was placed in the oil bath and the temperature of the content was increased to 215° C. while inside of the flask was stirred at 300 r/min. Once the temperature reaches 215° C., the stirring was temporarily stopped and a sample for analysis was taken, which was used as an intermediate mixture before cooling.

After that, the stirring was resumed and the flask was removed from the oil bath either partially or completely such that the rate for cooling the content is almost constant over time. The cooling rate was 4° C./minute at that time.

The cooling was continued until the temperature of the content becomes 140° C. After maintaining at 140° C. for 30 minutes, the stirring was temporarily terminated and a sample for analysis was taken, which was used as a final mixture after cooling. In Table 1, operating conditions (feeding amount of monoglyceride or the like) and the decomposition ratio of monoglyceride are listed.

Reference Example 3

To a 100-mL four-neck flask equipped with a stirrer and a thermometer, 25.0 g of the glycerin monostearic acid (glycerol monostearic acid manufactured by Wako Pure Chemical Industries, Ltd., monoglyceride content: 56% by mass) and 0.0026 g of calcium hydroxide (manufactured by Kanto Chemical Co., Inc.) were fed and the temperature was raised to 100° C. After dissolving glycerin monostearic acid, inside of the flask was stirred at 300 r/min so that calcium hydroxide can also homogeneously get dissolved.

After that, the flask was removed from the oil bath, and only the oil bath was heated to 220° C. After confirming that the oil bath temperature is stabilized, the flask was placed in the oil bath and the temperature of the content was increased to 215° C. while inside of the flask was stirred at 300 r/min. Once the temperature reaches 215° C., the stirring was temporarily stopped and a sample for analysis was taken, which was used as an intermediate mixture before cooling.

After that, the stirring was re-started and the flask was removed from the oil bath either partially or completely such that the rate for cooling the content is almost constant over time. The cooling rate was 16° C./minute at that time.

The cooling was continued until the temperature of the content becomes 140° C. After maintaining at 140° C. for 30 minutes, the stirring was temporarily terminated and a sample for analysis was taken, which was used as a final mixture after cooling. In Table 1, operating conditions (feeding amount of monoglyceride or the like) and the decomposition ratio of monoglyceride are listed.

TABLE 1

|  | Reference example 1 | Reference example 1 | Reference example 1 |
|---|---|---|---|
| feeding amount of monoglyceride [g] | 25.0 | 25.0 | 25.0 |
| feeding amount of glycerine [g] | 25.2 | 0 | 0 |
| Cooling rate [° C./minute] | 8 | 4 | 16 |
| Decomposition ratio of monoglyceride [mol %] | 0.80 | 5.4 | 3.8 |

Example 1

It was confirmed that, when the production method of the present invention is performed by using as a starting material the glycerin monostearic acid which has been obtained from Preparation Example 1, decomposition of the monoglyceride is suppressed and a mixture having a high content of fatty acid monoglyceride is obtained.

To a 100-mL four-neck flask equipped with a stirrer and a thermometer, 25.0 g of the glycerin monostearic acid containing the adjusted catalyst amount as obtained from Preparation Example 1 were fed and the temperature was raised to 100° C. After dissolving the raw materials, the flask was removed from the oil bath, and only the oil bath was heated to 220° C. After confirming that the oil bath temperature is stabilized, the flask was placed in the oil bath and the temperature of the content was increased to 215° C. while inside of the flask was stirred at 300 r/min. When the temperature reached 215° C., a sample for analysis was taken as an intermediate mixture before cooling.

After that, the stirring was resumed and 25.1 g of glycerin (purified glycerin manufactured by Kao Corporation), which had been preheated to 100° C., was added over five minutes while such control is made that the cooling rate of the content is almost constant over time. During and after addition of glycerin, the flask was partially or completely removed from the oil bath. The cooling rate at that time remained constant during and after addition of glycerin, which was 8° C./min. According to the addition of glycerin, the intermediate mixture was cooled to 175° C.

Even after completion of the addition of glycerin, cooling was continued until the temperature of the content becomes 140° C. After maintaining at 140° C. for 30 minutes, the stirring was temporarily terminated and a sample for analysis was taken from the top layer as a final mixture after cooling.

As a result of stopping the stirring, the content was separated into layers. In Table 2, operating conditions (feeding amount of monoglyceride or the like) and the decomposition ratio of monoglyceride are shown.

Comparative Example 1

To a 100-ml, four-neck flask equipped with a stirrer and a thermometer, 25.0 g of the glycerin monostearic acid containing the adjusted catalyst amount, which has been obtained from Preparation Example 1, were fed and the temperature was raised to 100° C. After dissolving the raw materials, the flask was removed, from the oil bath, and only the oil bath was heated to 220° C. After confirming that the oil bath temperature is stabilized, the flask was placed in the oil bath and the temperature of the content was increased to 215° C. while inside of the flask was stirred at 300 r/min. Once the temperature reaches 215° C., the stirring was temporarily stopped and a sample for analysis was taken as an intermediate mixture before decomposition.

After that, the stirring was resumed and the flask was removed from the oil bath either partially or completely such that the rate for cooling the content is almost constant over time. The cooling rate was 8° C./minute at that time. The cooling was continued until the temperature of the content becomes 140° C. After maintaining at 140° C. for 30 minutes, the stirring was temporarily terminated and a sample for analysis was taken as a final mixture after decomposition. In Table 2, operating conditions (feeding amount of monoglyceride or the like) and the decomposition ratio of monoglyceride are listed.

Comparative Example 2

To a 100-mL four-neck flask equipped with a stirrer and a thermometer, 25.0 g of the glycerin monostearic acid as obtained from Preparation Example 1 and 25.0 g of the glycerin (purified glycerin manufactured by Kao Corporation) were fed and the temperature was raised to 100° C. After dissolving the raw materials, the flask was removed from the oil bath, and only the oil bath was heated to 220° C. After confirming that the oil bath temperature is stabilized, the flask was placed in the oil bath and the temperature of the content was increased to 215° C. while inside of the flask was stirred at 300 r/min. Once the temperature reaches 215° C., the stirring was temporarily stopped and a sample for analysis was taken as an intermediate mixture before decomposition.

After that, the stirring was resumed, and after maintaining the content at 215° C. for 30 minutes, the stirring was temporarily stopped and a sample for analysis was taken from the top layer as a final mixture after decomposition. As a result of stopping the stirring, the content was separated into layers. In Table 2, operating conditions (feeding amount of monoglyceride or the like) and the decomposition ratio of monoglyceride are listed.

TABLE 2

| | Example 1 | Comparative example 1 | Comparative example 2 |
|---|---|---|---|
| feeding amount of monoglyceride [g] | 25.0 | 25.0 | 25.0 |
| feeding amount of glycerine [g] | 25.1 | 0 | 25.0 |
| Cooling rate [° C./minute] | 8 | 8 | No cooling |
| Decomposition ratio of monoglyceride [mol %] | 6.7 | 18 | 20 |

Based on the results of the decomposition ratio of monoglyceride in Example 1 and Comparative Example 1, it was found that the reverse reaction is suppressed by addition of glycerin, but not suppressed by cooling only.

Based on the results of the decomposition ratio of monoglyceride in Comparative Example 2, it was found that the decomposition ratio of monoglyceride becomes higher without cooling even when glycerin is added (that is, content of fatty acid monoglyceride is lowered).

Example 2

According to the same operations as Example 1, an intermediate mixture before cooling was obtained.

To the intermediate mixture, 12.5 g of glycerin (purified glycerin manufactured by Kao Corporation), which has been heated in advance to 40° C., was added over 0.3 minute. Before adding glycerin, the flask was completely removed from the oil bath. The cooling rate at that time was 130° C./minute. The temperature of the content was 175° C. when glycerin had been added.

After the completion of dropwise addition, the stirring was terminated. As a result of stopping the stirring, the content was separated into layers. A sample for analysis was collected from the top layer and used as a final mixture after decomposition. In Table 3, operating conditions (feeding amount of monoglyceride or the like) and the decomposition ratio of monoglyceride are listed.

Example 3

According to the same operations as Example 1, an intermediate mixture before cooling was obtained.

To the intermediate mixture, 25.0 g of the glycerin (manufactured by Kao Corporation, purified glycerin), which has been heated in advance to 40° C., was added over 0.5 minute. Before adding glycerin, the flask was completely removed from the oil bath. The cooling rate at that time was 130° C./minute. The temperature of the content was 150° C. when glycerin had been added.

After the completion of dropwise addition, the stirring was terminated. As a result of stopping the stirring, the content was separated into layers. A sample for analysis was collected from the top layer and used as a final mixture after cooling. In Table 3, operating conditions (feeding amount of monoglyceride or the like) and the decomposition ratio of monoglyceride are listed.

Example 4

According to the same operations as Example 1, an intermediate mixture before cooling was obtained.

To the intermediate mixture, 125 g of the glycerin (manufactured by Kao Corporation, purified glycerin), which has been heated in advance to 40° C., was added over 2.6 minutes. Before adding glycerin, the flask was completely removed from the oil bath. The cooling rate was 130° C./minute until the temperature of the content becomes 140° C. After that, it became difficult to have a constant cooling rate and the cooling rate has gradually decreased. When the addition of glycerin is completed, the temperature of the content was 90° C. The overall cooling rate, caused by the addition of glycerin, was 48° C./minute.

After the completion of dropwise addition, the stirring was terminated. As a result of stopping the stirring, the content was separated into layers. A sample for analysis was collected from the top layer and used as a final mixture after cooling. In Table 3, operating conditions (feeding amount of monoglyceride or the like) and the decomposition ratio of monoglyceride are listed.

TABLE 3

| | Example 2 | Example 3 | Example 4 |
|---|---|---|---|
| feeding amount of monoglyceride [g] | 25.0 | 25.0 | 25.0 |
| feeding amount of glycerine [g] | 12.5 | 25 | 125 |
| Cooling rate [° C./minute] | 130 | 130 | 48 (130*¹) |
| Decomposition ratio of monoglyceride [mol %] | 2.0 | 1.9 | 2.2 |

*[1]Cooling rate when the temperature of mixture was 140° C. or highrer.

Example 5

Production of Mixture Containing Fatty Acid Monoglyceride

The production apparatus illustrated in FIG. 1 was used. Each oblique line illustrated in FIG. 1 indicates a ribbon heater (RH).

<Step (i)>

To a 5-L, four-neck reaction vessel 10 equipped with a dehydrating tube-cooling tube, a thermometer, a tube for introducing nitrogen gas in addition to a stirrer 11, 538 g of glycerin (manufactured by Kishida Chemical Co., Ltd.) and 1460 g of LUNAC S-70V (mixture of fatty acids with carbon atom number of 16 and 18; manufactured by Kao Corporation) [glycerin/fatty acid (molar ratio)=1.1/1] were added, 1.00 g of calcium hydroxide (manufactured by Kanto Chemical Co., Inc.) was added, and the temperature was increased using a mantle heater while nitrogen stream was supplied at 20 mL/minute into the space of the liquid phase.

Once the raw materials are dissolved, inside of the reaction vessel 10 was stirred at 300 r/min. After confirming the discharge of water in the dehydrating tube, it was kept for 4 hours to allow the reaction to proceed. The final resultant temperature was 220° C. Based on gas chromatography analysis, it was found that the fatty acid concentration in the reaction product was 1.2% by mass and the ratio of the monoglyceride was 55% by mass to the total amount of esters.

The reactant was subjected to liquid transfer via the line 10a at 2.5 g/min with an aid of a plunger pump 21. Glycerin containing 0.05% by mass of calcium hydroxide in a vessel 12 was liquid-transported at a flow amount of 2.5 g/min via the line 12a with the plunger pump 22, and then both flows were mixed at the mixing point between the line 10a and the line 12a. Two liquids, after mixed, were subjected to temperature increase to 270° C. and reaction in the pre-heating tube and reaction tube, respectively.

<Step (ii)>

At the exit of the reaction tube, a pipe for glycerin transfer was connected, and the glycerin at 50° C. contained in a vessel 13 was subjected to liquid transfer at a flow amount of 5 g/min via the line 13a with an aid of a plunger pump 23 so that it can merge with the reaction solution. The liquid after the merge was recovered from the exit of the cooling tube. Liquid temperature at the exit of the cooling tube was 142° C.

The pre-heating tube was inner diameter of 1.8 mm×length of 2 m, the reaction tube was inner diameter 4.4 mm×length of 1.5 m, and the cooling tube was inner diameter of 1.8 mm×length of 1 m SUS316tube. They are connected to each other in series, and the pre-heating tube and the reaction tube were immersed in an oil bath. Temperature of the oil bath was 270° C. The cooling rate was 260° C./minute.

<Step (iii)>

As a result of keeping the recovered liquid which has been recovered from the exit of the cooling tube, the recovered liquid was separated into layers. From the oil layer of the recovered liquid, a sample for analysis was collected. Based on gas chromatography analysis, it was found that the ratio of the monoglyceride at that time was 69% by mass to the esters.

As it can be confirmed from the comparison with the results listed in Table 2, the results of Example 5 indicate that, by performing the production method of the present invention, the decomposition ratio of monoglyceride in a mixture is lowered and the content of fatty acid monoglyceride is increased.

The invention claimed is:

1. A method for producing a mixture comprising fatty acid monoglyceride from glycerin and a compound having at least one acyl group, selected from the group consisting of fatty acids and fatty acid glycerides, comprising:
   (i) a step of obtaining a mixture comprising fatty acid monoglyceride by heating and reacting glycerin and a compound having at least one acyl group, selected from the group consisting of fatty acids and fatty acid glycerides in the presence of a catalyst,
   (ii) a cooling step comprising adding glycerin, which is liquid and has a lower temperature than a temperature of the mixture, to the mixture to cool the mixture, and
   (iii) a step of separating the mixture comprising fatty acid monoglyceride from glycerin, obtained in the step (ii), by separating layers.

2. The method for producing a mixture comprising fatty acid monoglyceride according to claim 1, wherein the addition amount of glycerin in the step (ii) is 1 part by mass or more and 1000 parts by mass or less per 100 parts by mass of the mixture comprising fatty acid monoglyceride obtained in the previous step.

3. The method for producing a mixture comprising fatty acid monoglyceride according to claim 1, wherein the rate of cooling the mixture in the step (ii) is 1° C./minute or higher and 1000° C./minute or lower.

4. The method for producing a mixture comprising fatty acid monoglyceride according to claim 1, wherein the addition amount of glycerin in the step (ii) is $1 \times 10^3$ parts by mass or more and $1 \times 10^9$ parts by mass or less per 100 parts by mass of the catalyst used in the previous step.

5. The method for producing a mixture comprising fatty acid monoglyceride according to claim 1, wherein a reaction temperature in the step (i) is 200° C. or higher and 400° C. or lower.

6. The method for producing a mixture comprising fatty acid monoglyceride according to claim 1, wherein the temperature of glycerin to be added in the step (ii) is 0° C. or higher and 180° C. or lower.

7. The method for producing a mixture containing fatty acid monoglyceride according to claim 1, wherein the step (ii) is a step for mixing the mixture comprising fatty acid monoglyceride and glycerin while continuously transporting them separately from each other.

8. The method for producing a mixture comprising fatty acid monoglyceride according to claim 1, wherein the glycerin separated in the step (iii) is used in the step (i) or the step (ii).

9. The method for producing a mixture comprising fatty acid monoglyceride according to claim 1, wherein the catalyst used in the step (i) is an alkali metal hydroxide or an alkaline earth metal hydroxide.

10. The method for producing a mixture comprising fatty acid monoglyceride according to claim 1, wherein the catalyst concentration of the catalyst used in the step (i) is 1 ppm or more and 1000 ppm or less.

11. The method for producing a mixture comprising fatty acid monoglyceride according to claim 1, wherein the separation method of the step (iii) by separating layers is stationary separation.

12. The method for producing a mixture comprising fatty acid monoglyceride according to claim 1, wherein a catalyst concentration in a liquid phase of the mixture is lowered by adding glycerin and the catalyst contained in the mixture is extracted.

13. The method for producing a mixture comprising fatty acid monoglyceride according to claim 1, wherein a rate of cooling the mixture in the step (ii) is 5° C./minute or higher and 1000° C./minute or lower.

14. The method for producing a mixture comprising fatty acid monoglyceride according to claim 1, wherein a rate of cooling the mixture in the step (ii) is 8° C./minute or higher and 1000° C./minute or lower.

15. The method for producing a mixture comprising fatty acid monoglyceride according to claim 1, wherein a rate of cooling the mixture in the step (ii) is 50° C./minute or higher and 1000° C./minute or lower.

16. The method for producing a mixture comprising fatty acid monoglyceride according to claim 1, wherein a rate of cooling the mixture in the step (ii) is 100° C./minute or higher and 1000° C./minute or lower.

17. The method for producing a mixture comprising fatty acid monoglyceride according to claim 1, wherein the mixture is cooled by adding glycerine in the step (ii) until the temperature of the mixture is 140° C. or lower.

18. The method for producing a mixture comprising fatty acid monoglyceride according to claim 1, wherein a content of glycerin in the step (i) is 1.0 mol or more and 5.0 mol or less per mol of an acyl group of the compound having an acyl group.

19. The method for producing a mixture comprising fatty acid monoglyceride according to claim 1, wherein the temperature of the mixture, obtained from the step (i) and used in the step (ii), is a reaction temperature of the step (i).

20. The method for producing a mixture comprising fatty acid monoglyceride according to claim 1, wherein a time for the reaction between glycerin and the compound having an acyl group in the step (i) is 5 minutes or longer and 12 hours or shorter.

* * * * *